(12) United States Patent
Mortell et al.

(10) Patent No.: US 6,984,279 B2
(45) Date of Patent: Jan. 10, 2006

(54) PROCESS TO MAKE BOXER SHORTS WITH AN ABSORBENT CORE

(75) Inventors: Heather Schenck Mortell, Neenah, WI (US); Joseph Daniel Coenen, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 60 days.

(21) Appl. No.: 10/303,637

(22) Filed: Nov. 25, 2002

(65) Prior Publication Data

US 2004/0102746 A1    May 27, 2004

(51) Int. Cl.
 *B32B 31/00*    (2006.01)
(52) U.S. Cl. .................. 156/211; 156/73.1; 156/197; 156/217; 156/227; 156/258; 156/270; 156/304.6; 156/308.4; 156/513
(58) Field of Classification Search ............. 156/258, 156/256, 270, 197, 211, 217, 221, 226, 227, 156/73.1, 304.1, 304.6, 513
See application file for complete search history.

(56) References Cited

U.S. PATENT DOCUMENTS

| | | |
|---|---|---|
| 478,281 A | 7/1892 | Hamilton et al. |
| 1,577,409 A | 3/1926 | Rand |
| 1,664,298 A | 3/1928 | Katz |
| 1,971,558 A | 8/1934 | Goodman |
| 2,030,306 A | 2/1936 | Lain |
| 2,032,982 A | 3/1936 | Gerstman |
| 2,088,302 A | 7/1937 | McKeever |
| 2,116,822 A | 5/1938 | Berger |
| 2,242,526 A | 5/1941 | Kneibler |
| 2,252,019 A | 8/1941 | Meinecke et al. |
| 2,319,138 A | 5/1943 | Kneibler |
| 2,391,641 A | 12/1945 | O'Hern |
| 2,435,945 A | 2/1948 | Redmond |
| 2,450,789 A | 10/1948 | Frieman |
| 2,522,510 A | 9/1950 | Fridolph |
| 2,538,596 A | 1/1951 | Sheridan |
| 2,675,806 A | 1/1954 | Bram |
| 2,711,735 A | 6/1955 | Sabo |

(Continued)

FOREIGN PATENT DOCUMENTS

AT    168478    6/1951

(Continued)

OTHER PUBLICATIONS

Printed materials (3 pages) showing pull-on diapers disclosed at a trade show Apr. 27-29, 2004 in Miami Beach, Florida, U.S.A.

(Continued)

*Primary Examiner*—Linda Gray
(74) *Attorney, Agent, or Firm*—Pauley Petersen & Erickson

(57) ABSTRACT

A method of making a pant having a front-to-back crotch seam includes providing a flat web. The flat web can be cut into separate pieces or cut to provide interconnected pieces and the center portion of each separate piece is removed. Slits are cut in each separate piece or each interconnected piece and the remaining attached segments are drawn away from each other in opposite directions to bring first and second seam edges together for the purpose of forming a garment shell with a crotch seam. The method may be applied to a single piece of material representing a single garment or to an interconnected web of garments. After forming the crotch seam, the garment shell can be folded and side seams formed. The pant may include an absorbent structure.

20 Claims, 11 Drawing Sheets

U.S. PATENT DOCUMENTS

| | | |
|---|---|---|
| 2,838,047 A | 6/1958 | Sidnell |
| 2,842,129 A | 7/1958 | Ernstorff |
| 2,859,752 A | 11/1958 | Haber |
| 3,245,407 A | 4/1966 | Mason |
| 3,338,992 A | 8/1967 | Kinney |
| 3,341,394 A | 9/1967 | Kinney |
| 3,418,660 A | 12/1968 | Shumate |
| 3,502,538 A | 3/1970 | Petersen |
| 3,502,763 A | 3/1970 | Hartmann |
| 3,542,615 A | 11/1970 | Dobo et al. |
| 3,611,443 A | 10/1971 | Braun |
| 3,648,699 A | 3/1972 | Anderson et al. |
| 3,678,516 A | 7/1972 | Backer |
| 3,692,618 A | 9/1972 | Dorschner et al. |
| 3,714,946 A | 2/1973 | Rudes |
| 3,739,398 A | 6/1973 | Sarmiento |
| 3,802,817 A | 4/1974 | Matsuki et al. |
| 3,806,007 A | 4/1974 | Grantham |
| 3,844,282 A | 10/1974 | King |
| 3,859,667 A | 1/1975 | Roy |
| 3,869,999 A | 3/1975 | Richter |
| 3,920,237 A | 11/1975 | Grantham |
| 4,059,257 A | 11/1977 | Grantham |
| 4,081,301 A | 3/1978 | Buell |
| 4,100,324 A | 7/1978 | Anderson et al. |
| 4,114,621 A | 9/1978 | Mims, Jr. |
| 4,145,763 A | 3/1979 | Abrams et al. |
| 4,227,952 A | 10/1980 | Sabee |
| 4,280,230 A | 7/1981 | LaFleur |
| 4,284,454 A | 8/1981 | Joa |
| 4,300,241 A | 11/1981 | Shaull |
| 4,310,929 A | 1/1982 | Finlay |
| 4,327,448 A | 5/1982 | Lunt |
| 4,338,939 A | 7/1982 | Daville |
| 4,340,563 A | 7/1982 | Appel et al. |
| 4,368,565 A | 1/1983 | Schwarz |
| 4,392,259 A | 7/1983 | Bredo |
| 4,397,704 A | 8/1983 | Frick |
| 4,417,938 A | 11/1983 | Sigl |
| 4,449,254 A | 5/1984 | Fogg |
| 4,555,245 A | 11/1985 | Armbruster |
| 4,597,110 A | 7/1986 | Smith, Sr. et al. |
| 4,608,115 A | 8/1986 | Schroth et al. |
| 4,644,945 A | 2/1987 | Thorner |
| 4,646,362 A | 3/1987 | Heran et al. |
| 4,650,530 A * | 3/1987 | Mahoney et al. .......... 156/73.1 |
| 4,655,760 A | 4/1987 | Morman et al. |
| 4,663,106 A | 5/1987 | Pomplun et al. |
| 4,663,220 A | 5/1987 | Wisneski et al. |
| 4,665,306 A | 5/1987 | Roland et al. |
| 4,671,793 A | 6/1987 | Hults et al. |
| 4,675,918 A | 6/1987 | O'Brien |
| 4,704,116 A | 11/1987 | Enloe |
| 4,745,636 A | 5/1988 | Lunt |
| 4,771,483 A | 9/1988 | Hooreman et al. |
| 4,786,346 A | 11/1988 | Ales et al. |
| 4,805,243 A | 2/1989 | Gibbens et al. |
| 4,816,094 A | 3/1989 | Pomplun et al. |
| 4,835,795 A | 6/1989 | Lonon |
| 4,847,134 A | 7/1989 | Fahrenkrug et al. |
| 4,870,958 A | 10/1989 | Webster |
| 4,872,221 A | 10/1989 | Stone, III |
| 4,875,240 A | 10/1989 | Barrett |
| 4,883,549 A | 11/1989 | Frost et al. |
| 4,892,536 A | 1/1990 | DesMarais et al. |
| 4,895,568 A | 1/1990 | Enloe |
| 4,935,021 A | 6/1990 | Huffman et al. |
| 4,946,539 A | 8/1990 | Ales et al. |
| 4,955,880 A | 9/1990 | Rodriquez |
| 4,964,860 A | 10/1990 | Gipson et al. |
| D315,050 S | 3/1991 | Bush et al. |
| 5,014,364 A | 5/1991 | Orr |
| 5,022,240 A | 6/1991 | Peleg |
| 5,046,272 A | 9/1991 | Vogt et al. |
| 5,052,058 A | 10/1991 | Mueller |
| 5,067,178 A | 11/1991 | Katchka |
| 5,087,253 A | 2/1992 | Cooper |
| 5,103,505 A | 4/1992 | Llorens |
| 5,135,522 A | 8/1992 | Fahrenkrug et al. |
| 5,171,388 A | 12/1992 | Hoffman et al. |
| 5,187,817 A | 2/1993 | Zolner |
| 5,210,882 A | 5/1993 | Moretz et al. |
| 5,217,782 A | 6/1993 | Moretz et al. |
| 5,226,992 A | 7/1993 | Morman |
| D341,243 S | 11/1993 | Costella et al. |
| 5,297,296 A | 3/1994 | Moretz et al. |
| 5,303,424 A | 4/1994 | Cromartie |
| 5,306,536 A | 4/1994 | Moretz et al. |
| 5,315,716 A | 5/1994 | Baum |
| 5,315,717 A | 5/1994 | Moretz et al. |
| 5,370,634 A | 12/1994 | Ando et al. |
| 5,379,462 A | 1/1995 | Morgan et al. |
| 5,382,246 A | 1/1995 | Kawano |
| 5,435,014 A | 7/1995 | Moretz et al. |
| 5,445,628 A | 8/1995 | Gipson et al. |
| 5,500,063 A | 3/1996 | Jessup |
| 5,545,158 A | 8/1996 | Jessup |
| 5,549,593 A | 8/1996 | Ygge et al. |
| 5,556,504 A | 9/1996 | Rajala et al. |
| 5,566,392 A | 10/1996 | Dzelzkalns |
| D377,557 S | 1/1997 | Jagger |
| 5,649,913 A | 7/1997 | Cohen |
| D382,386 S | 8/1997 | Malone |
| 5,669,902 A | 9/1997 | Sivilich |
| 5,669,996 A | 9/1997 | Jessup |
| 5,690,626 A | 11/1997 | Suzuki et al. |
| 5,690,627 A | 11/1997 | Clear et al. |
| 5,716,478 A | 2/1998 | Boothe et al. |
| 5,718,003 A | 2/1998 | Gwinn |
| 5,733,401 A * | 3/1998 | Linman et al. .............. 156/160 |
| 5,746,730 A | 5/1998 | Suzuki et al. |
| 5,755,902 A | 5/1998 | Reynolds |
| 5,759,340 A | 6/1998 | Boothe et al. |
| 5,790,983 A | 8/1998 | Rosch et al. |
| 5,827,260 A | 10/1998 | Suzuki et al. |
| 5,853,405 A | 12/1998 | Suprise |
| 5,876,394 A | 3/1999 | Rosch et al. |
| 5,891,122 A | 4/1999 | Coates |
| D408,964 S | 5/1999 | Hernandez |
| 5,906,604 A | 5/1999 | Rönnberg et al. |
| 5,906,879 A | 5/1999 | Huntoon et al. |
| 5,907,872 A | 6/1999 | Alberts et al. |
| 5,921,974 A | 7/1999 | Kikuchi |
| 5,953,754 A | 9/1999 | Rosch et al. |
| 5,956,774 A | 9/1999 | Mackley |
| 5,978,971 A | 11/1999 | Wald |
| D417,940 S | 12/1999 | Coates et al. |
| 6,009,558 A | 1/2000 | Rosch et al. |
| 6,010,586 A | 1/2000 | Suprise |
| 6,018,822 A | 2/2000 | Hernandez |
| 6,022,443 A | 2/2000 | Rajala et al. |
| 6,105,171 A | 8/2000 | Niedermeyer |
| 6,142,983 A | 11/2000 | Suprise et al. |
| 6,145,132 A | 11/2000 | Towner |
| 6,149,637 A | 11/2000 | Allen et al. |
| 6,149,755 A | 11/2000 | McNichols et al. |
| 6,168,585 B1 | 1/2001 | Cesco-Cancian |
| 6,174,303 B1 | 1/2001 | Suprise et al. |
| 6,192,521 B1 | 2/2001 | Alberts et al. |
| 6,205,592 B1 | 3/2001 | Gouws |
| 6,248,097 B1 | 6/2001 | Beitz et al. |
| 6,287,169 B1 | 9/2001 | Willms et al. |
| 6,289,519 B1 | 9/2001 | Murakami et al. |
| 6,293,934 B1 | 9/2001 | Kumasaka |

| | | | | | | |
|---|---|---|---|---|---|---|
| 6,293,936 | B1 | 9/2001 | Otsubo | FR | 1.276.791 | 10/1961 |
| 6,293,937 | B2 | 9/2001 | Matsushita et al. | GB | 238557 | 8/1926 |
| 6,308,339 | B1 | 10/2001 | Murakami et al. | GB | 307652 | 3/1929 |
| 6,312,420 | B1 | 11/2001 | Sasaki et al. | GB | 571098 | 8/1945 |
| 6,319,347 | B1 | 11/2001 | Rajala et al. | GB | 620555 | 3/1949 |
| 6,342,050 | B1 | 1/2002 | Rönnberg et al. | GB | 701081 | 12/1953 |
| 6,368,312 | B1 | 4/2002 | Otsubo | GB | 1 342 022 | 12/1973 |
| D456,995 | S | 5/2002 | Baker | GB | 2 069 820 A | 9/1981 |
| 6,463,591 | B1 | 10/2002 | Toratani | GB | 2 112 268 | 7/1983 |
| 6,475,201 | B2 | 11/2002 | Saito et al. | GB | 2 196 525 | 5/1988 |
| 6,516,473 | B2 | 2/2003 | Saito | GB | 2 208 263 | 3/1989 |
| 6,539,554 | B1 | 4/2003 | Portela | GB | 2 269 978 | 3/1994 |
| 6,560,786 | B2 | 5/2003 | Lipton | GB | 2 269 998 | 3/1994 |
| 6,585,840 | B2 | 7/2003 | Rabe et al. | GB | 2 269 999 | 3/1994 |
| 6,626,883 | B2 | 9/2003 | Wada et al. | GB | 2 327 859 | 2/1999 |
| 6,666,851 | B2 | 12/2003 | Otsubo et al. | JP | 2000 355801 | 12/2000 |
| 2001/0014798 | A1 | 8/2001 | Fernfors | JP | 2001 172801 | 6/2001 |
| 2001/0044614 | A1 | 11/2001 | Damay et al. | JP | 2001 172802 | 6/2001 |
| 2002/0000291 | A1 | 1/2002 | Coenen et al. | JP | 3177341 | 6/2001 |
| 2002/0002021 | A1 | 1/2002 | May et al. | JP | 2001 204762 | 7/2001 |
| 2002/0002358 | A1 | 1/2002 | Durrance et al. | JP | 2001 204764 | 7/2001 |
| 2002/0009940 | A1 | 1/2002 | May et al. | JP | 2001 204765 | 7/2001 |
| 2002/0084017 | A1 | 7/2002 | Rabe et al. | JP | 3182069 | 7/2001 |
| 2002/0087137 | A1 | 7/2002 | Christoffel et al. | JP | 2001 207301 | 8/2001 |
| 2002/0099345 | A1 | 7/2002 | Saito et al. | JP | 2001 224615 | 8/2001 |
| 2003/0109842 | A1 | 6/2003 | Louis et al. | JP | 2001 238909 | 9/2001 |
| 2003/0115660 | A1 | 6/2003 | Hopkins | JP | 2001 245929 | 9/2001 |
| 2004/0098791 | A1 | 5/2004 | Faulks | JP | 2001 248002 | 9/2001 |
| 2004/0107481 | A1 | 6/2004 | Mortell et al. | JP | 2001 254202 | 9/2001 |
| 2004/0116881 | A1 | 6/2004 | Nordness et al. | JP | 2001 262402 | 9/2001 |

FOREIGN PATENT DOCUMENTS

| | | | |
|---|---|---|---|
| CA | 2356510 A1 | 2/2003 | |
| DE | 435 579 | 2/1927 | |
| DE | 809 844 | 8/1951 | |
| DE | 839 244 | 5/1952 | |
| DE | 101 44 255 | 2/2003 | |
| DE | 101 44 255 C1 | 2/2003 | |
| EP | 217 032 | 4/1987 | |
| EP | 0 717 971 | 6/1996 | |
| EP | 763 353 | 3/1997 | |
| EP | 549 988 | 6/1998 | |
| EP | 904 758 | 3/1999 | |
| EP | 911 006 | 4/1999 | |
| EP | 0 925 729 A2 | 6/1999 | |
| EP | 933 072 | 8/1999 | |
| EP | 1 048 231 | 11/2000 | |
| EP | 1 060 677 | 12/2000 | |
| EP | 1 060 679 | 12/2000 | |
| EP | 1 108 371 | 6/2001 | |
| EP | 1 108 372 | 6/2001 | |
| EP | 1 108 373 | 6/2001 | |
| EP | 1 110 463 | 6/2001 | |
| EP | 1 118 277 | 7/2001 | |
| EP | 1 125 571 | 8/2001 | |
| EP | 1 159 883 | 12/2001 | |
| EP | 1 166 730 | 1/2002 | |
| EP | 1 179 302 | 2/2002 | |
| EP | 1 184 012 | 3/2002 | |
| EP | 1 188 427 | 3/2002 | |
| FR | 1.276.791 | 10/1960 | |
| JP | 3205643 | 9/2001 | |
| JP | 3205690 | 9/2001 | |
| JP | 3208258 | 9/2001 | |
| JP | 2001 299813 | 10/2001 | |
| JP | 3221601 | 10/2001 | |
| JP | 2001 309946 | 11/2001 | |
| JP | 2001 333932 | 12/2001 | |
| JP | 2002-320641 | 11/2002 | |
| JP | 2004 159949 | 6/2004 | |
| WO | 95/16421 | 6/1995 | |
| WO | 95/18589 | 7/1995 | |
| WO | 96/03950 | 2/1996 | |
| WO | WO 97/02797 | 1/1997 | |
| WO | 99/33421 | 7/1999 | |
| WO | WO 01/03524 | 1/2001 | |
| WO | 01/58401 | 8/2001 | |
| WO | 01/61093 | 8/2001 | |
| WO | 01/67900 | 9/2001 | |
| WO | 01/87217 | 11/2001 | |
| WO | 01/87218 | 11/2001 | |
| WO | 01/87562 | 11/2001 | |
| WO | 01/87753 | 11/2001 | |
| WO | 01/88245 | 11/2001 | |
| WO | 02/49565 | 6/2002 | |
| WO | 02/52967 | 7/2002 | |
| WO | WO 03/057107 A1 | 7/2003 | |

OTHER PUBLICATIONS

US 5,915,536, 06/1999, Alberts et al. (withdrawn)

* cited by examiner

PROCESS TO MAKE BOXER SHORTS WITH AN ABSORBENT CORE

BACKGROUND OF THE INVENTION

The present invention pertains to methods of making pants having front-to-back crotch seams. More particularly, the present invention pertains to methods of making boxer shorts having front-to-back crotch seams. The boxer shorts may be absorbent or non-absorbent.

Pant-like garments have numerous applications including disposable clothing, training pants, feminine care products, adult incontinence products, disposable swimwear, or the like. Pant-like disposable garments are typically three-dimensional products with closed sides so that the product has a unitary waist opening and two leg openings. The wearer raises and lowers the garment to apply the product. Three-dimensional, boxer shorts-like products are particularly appealing because the boxer shorts look more like conventional articles of clothes.

Many disposable pants are formed as composite structures in which several components are combined to form a product specifically suited to its intended purpose. For example, disposable pants often include one or more absorbent materials intended to absorb various bodily exudates such as urine, menstrual fluid, and/or sweat. Such products may include a liquid permeable bodyside liner and a liquid impermeable outer cover, and can include other materials and features such as elastic materials and containment structures.

However, many disposable pants can be aesthetically unappealing. Existing disposable absorbent pants can often be overly bulky and can often resemble disposable baby diapers. Various attempts have been made to provide disposable pants having an improved, more clothing-like appearance. However, disposable pants, particularly disposable absorbent boxer shorts, present many manufacturing challenges. In part, this is due to the high speed that is necessary to economically produce relatively low-cost disposable absorbent products. Product design can often be compromised by cost and manufacturing constraints, resulting in disposable pants that lack aesthetic appeal and product function.

U.S. Pat. No. 6,293,936 issued Sep. 25, 2001 to Otsubo and assigned to Uni-Charm Corporation, and European Patent Application Nos. EP 1 048 231 and 1 108 372 by Uni-Charm Co. Limited describe boxer shorts. However, these Uni-Charm references do not disclose making boxer shorts from a flat web. Instead, multiple web pieces are seamed together resulting in a three-dimensional garment that may be difficult to handle at the speeds of modem manufacturing equipment.

Thus, what is lacking and needed in the art are garment-like, aesthetically appealing boxer shorts, as well as methods of efficiently manufacturing such boxer shorts.

SUMMARY OF THE INVENTION

In response to the above-referenced unfulfilled need in the art, new pants, and methods for manufacturing such pants, have been invented. The material for the garment shell of the pant is handled as a flat web throughout assembly until seaming in order to streamline the assembly.

One aspect of the invention pertains to a method of making a pant having a front-to-back crotch seam. One embodiment of the method comprises: providing a flat web defining a center portion; cutting out the center portion of the flat web to define a first seam edge and a second seam edge; cutting at least one slit to define a first attached segment, and at least one slit to define a second attached segment; drawing the first and second attached segments away from each other; bringing the first seam edge toward the second seam edge; bonding the first and second seam edges together to form the crotch seam; and attaching a front region to a back region to form at least two side seams. The method can be carried out using machine direction assembly or cross-machine direction assembly. In addition, the method can include the step of attaching an absorbent structure.

In another aspect of the invention, the flat web may be cut to provide interconnected pieces prior to drawing the attached segments away from each other. The garment shells can remain interconnected until after formation of the crotch seam.

Another aspect of the present invention pertains to a pant made from a single flat web and having a front-to-back crotch seam. One embodiment of the pant comprises: a garment shell including a front region, a back region and a crotch region, with a front-to-back crotch seam extending through the front region, the back region and the crotch region. The pant may also include an absorbent structure.

The present invention relates to a wide variety of absorbent and non-absorbent pants, including training pants, swim pants, diaper pants, incontinence garments, feminine care products, health care garments, apparel for institutional, industrial and consumer use, or other garments. Disposable absorbent pants are adapted to be worn adjacent the body of a wearer to absorb and contain various exudates discharged from the body.

DEFINITIONS

Figure 1:
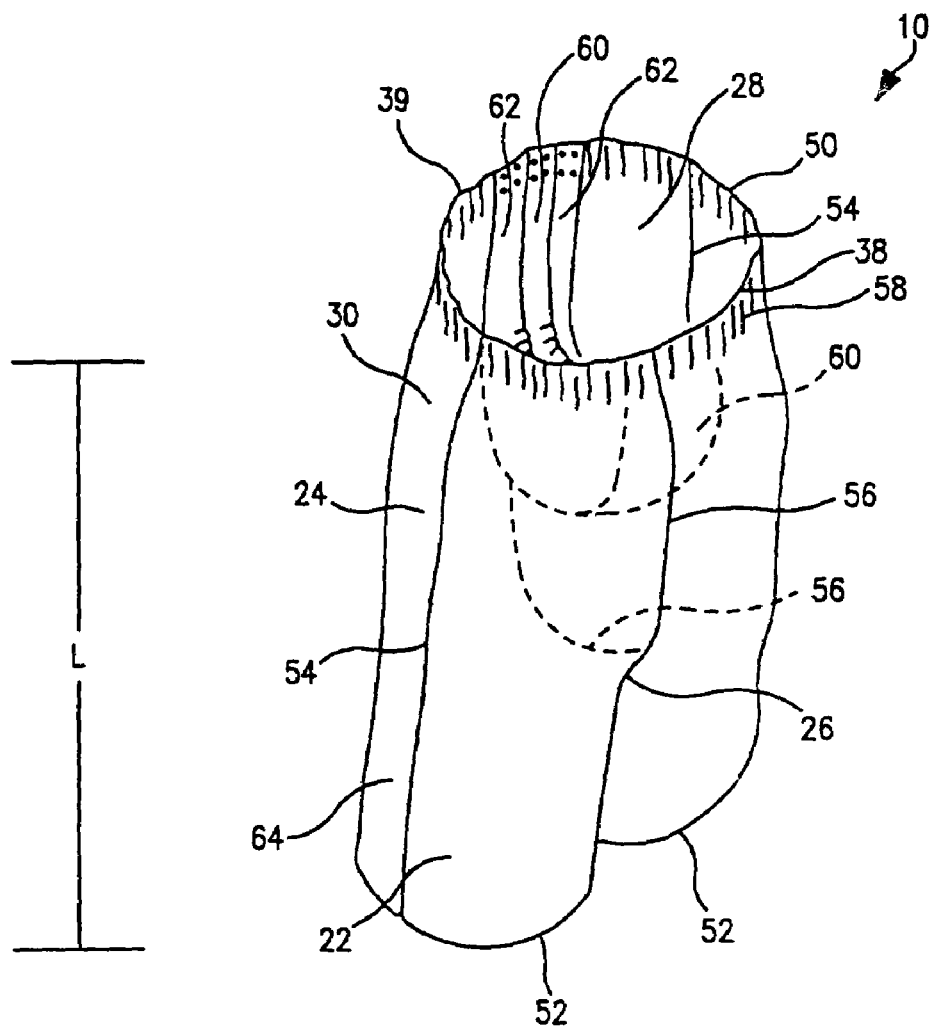
FIG. 1 is a perspective view of one embodiment of a pant according to the present invention.

Within the context of this specification, each term or phrase below will include the following meaning or meanings.

"Attached" refers to the joining, adhering, connecting, bonding, sewing together, or the like, of two elements. Two elements will be considered to be attached together when they are attached directly to one another or indirectly to one another, such as when each is directly attached to intermediate elements. The term "attached" includes permanent and refastenable attachment. In addition, the attachment can be completed either during the manufacturing process or by the end user.

"Bonded" refers to the joining, adhering, connecting, attaching, sewing together, or the like, of two elements. Two elements will be considered to be bonded together when they are bonded directly to one another or indirectly to one another, such as when each is directly bonded to intermediate elements.

"Boxer shorts" refers to a pant, trunks, briefs, and the like, that are relatively loose fitting at the leg area.

"Comprising" is inclusive or open-ended and does not exclude additional, unrecited elements or method steps.

"Connected" refers to the joining, adhering, bonding, attaching, sewing together, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all woven, knitted and nonwoven fibrous webs.

"Flat web" comprises any material used for making garments that can be provided and processed in a substantially open, unfolded state; while the web can possess ripples or areas that do not lie exactly within an overall plane of the web, all points of the web should be reasonably identifiable as constituents in either an upper or a lower surface of the web. No portions of a flat web are enclosed or fixed into a loop or tunnel-like, or three-dimensional configuration.

"Front-to-back crotch seam" refers to a seam traveling from the front region to the back region of a pant-style garment, through the crotch region. The seam can join two separate pieces of material, or separate edges of a single piece of material.

"Garment shell" refers to an outer cover or outer layer of a garment. In a single-ply garment, the single layer of the garment is the garment shell.

"Garment insert" refers to an inner layer of a garment. The garment insert provides a close-to-the-body fit about a wearer's lower torso, thereby serving as a form of built-in underwear within the garment.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Machine direction" refers to the length of a fabric in the direction in which it is produced, as opposed to "cross-machine direction" which refers to the width of a fabric in a direction generally perpendicular to the machine direction.

Figure 6:
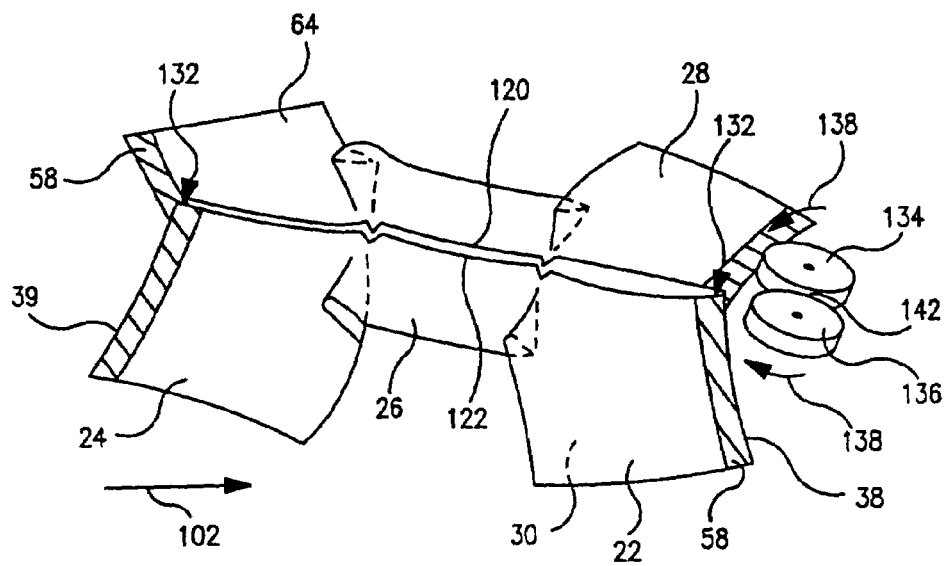
FIG. 6 illustrates the garment shell according to one embodiment of the invention prior to forming the crotch seam.
Figure 6A:
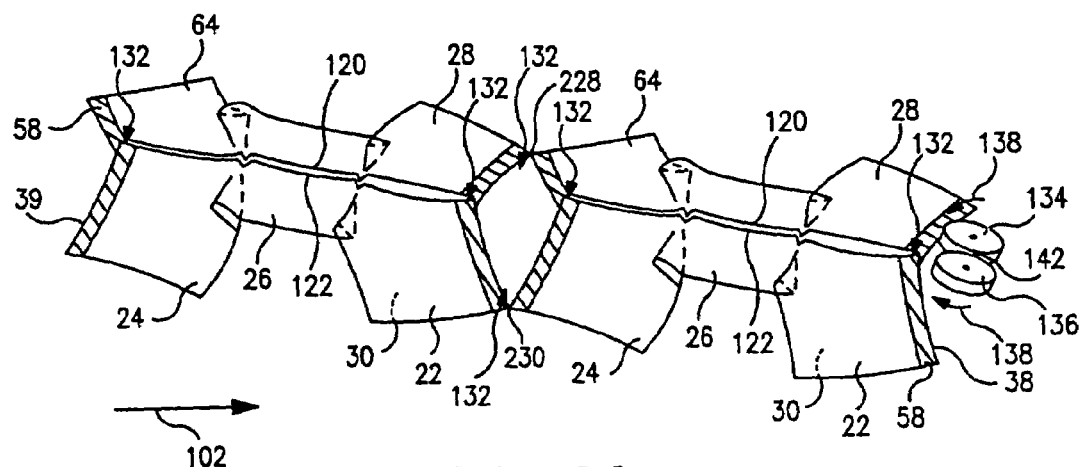
FIG. 6A illustrates interconnected garment shells prior to formation of the crotch seam.

"Machine direction assembly" refers to a manufacturing process in which disposable products travel in an end-to-end or waist-to-waist orientation, in the longitudinal direction shown by arrow 102 in FIGS. 6 and 6A. A process utilizing a machine direction assembly entails products traveling through a converting machine parallel to the direction of arrow 102, as opposed to "cross-machine direction assembly" in which the products travel in a side-by-side orientation such as that shown by arrow 302 in FIGS. 9–13.

"Member" when used in the singular can have the dual meaning of a single element or a plurality of elements.

"Nonwoven" and "nonwoven web" and "web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Pants" includes full length and short pants.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

"Three-dimensional garment" refers to a garment that cannot be laid flat with all of its seams in one plane.

"Total recovery", or variations thereof, refers to a material recovering to generally within about 20 percent of its relaxed, preextended dimension.

These terms may be defined with additional language in the remaining portions of the specification.

DETAILED DESCRIPTION OF THE PREFERRED EMBODIMENTS

As representatively illustrated in FIG. 1, an embodiment of a pant 10 of the present invention includes a garment shell 64. The garment shell 64 can include a front region 22, a back region 24, a crotch region 26, an inner surface 28 which is configured to contact the wearer, and an outer surface 30 opposite the inner surface 28 which is configured to face away from the surface of the wearer's body. The pant 10 also defines a pair of longitudinally opposed waist edges, which are designated front waist edge 38 and back waist edge 39. The front region 22 is contiguous with the front waist edge 38, and the back region 24 is contiguous with the back waist edge 39. The front region 22 includes the portion of the pant 10 which, when worn, is positioned on the front of the wearer while the back region 24 includes the portion of the pant 10 which, when worn, is positioned on the back of the wearer. The crotch region 26 of the pant 10 includes the portion of the pant which, when worn, is positioned between the legs of the wearer and covers the lower torso of the wearer. As illustrated in FIG. 1, the front and back regions 22 and 24 are joined together at side seams 54 and the left and right sides of the pant 10 are joined together at the crotch seam 56 to define a three-dimensional pant configuration having a waist opening 50 and a pair of leg openings 52. In particular embodiments, the pant 10 can include an absorbent structure 60. Various embodiments of these and other features will now be described.

In particular embodiments, the crotch seam 56 follows a path which begins substantially at the front waist edge 38, extends through the crotch region 26, and terminates substantially at the back waist edge 39. In alterative embodiments, the crotch seam 56 can follow a path which begins below the front waist edge 38 on the front region 22 and terminates below the back waist edge 39 on the back region 24. As is known in the art, the crotch seam 56 can be an inward fin seam or a lap seam (not shown). In the alternative, the crotch seam 56 can be an outward fin seam.

The pant 10 also includes side seams 54 which connect the front region 22 to the back region 24 to create the pant 10. The side seams 54 can take any number of forms, including both refastenable and non-refastenable seams as is known in the art. The provision of the side seams 54 can be accomplished in the manner described in U.S. Pat. No. 5,046,272, issued Sep. 10, 1991 to Vogt et al., which is incorporated herein by reference, or in the manner described in PCT Publications WO 01/87562 by Tomsovic, et al., WO 01/87217 by Durrance, et al., WO 01/87753 by Csida et al., and or WO 01/87218 by Vogt, et al., all of which which are incorporated herein by reference. As is known in the art, the side seams 54 can be inward or outward fin seams or lap seams (not shown). It is contemplated that the side seams 54 may be located only at the waist opening 50, leaving a slit open above the leg openings 52, such as in the style of some running or athletic garments. Alternatively, side seams 54 may extend fully from waist opening 50 to respective leg openings 52.

The pant 10 can also have a waist elastic member 58. The waist elastic member 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic member 58 includes a plurality of dry-spun coalesced multifilament spandex elastomeric threads sold under the trade name LYCRA® and available from E.I. du Pont de Nemours and Company, Wilmington, Del., U.S.A. In particular embodiments, the elastic material includes a stretch-thermal laminate (STL), a neck-bonded laminated (NBL), a reversibly necked laminate, or a stretch-bonded laminate (SBL) material. Methods of making such STL, NBL and SBL materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the names of Taylor et al.; PCT Publication WO 01/88245 published on Nov. 22, 2001 in the names of Welch, et al.; all of which are incorporated herein by reference. Alternatively, the waist elastic member 58 can include other woven or nonwoven materials, such as stretchable but inelastic materials.

As another alternative, the waist elastic member 58 can be a material exhibiting delayed retraction, or can in fact be non-elastic. Delayed retraction materials may include those designed to retract relatively slowly following compression, such as "temporarily inhibited" elastic materials. "Temporarily inhibited" materials are described, for example, in U.S. Pat. No. 5,545,158 issued Aug. 13, 1996, to Jessup, U.S. Pat. No. 5,669,996 issued Sep. 23, 1997, to Jessup, and U.S. Pat. No. 5,500,063 issued Mar. 19, 1996, to Jessup, all of which are herein incorporated by reference, and references cited therein. Alternatively, a delayed retraction material may be designed to resist retraction until an activation process occurs, such as so-called "latent elastic" materials. Suitable retractive materials for use as a delayed retraction material can alternatively comprise any material adapted to retract upon activation, whether immediately upon activation or subsequently thereto. The retractive material can comprise elastomeric or nonelastomeric materials. Suitable nonelastomeric retractive materials can comprise without limitation polyether block amides (PEBAX®) or the like, and laminates thereof. Suitable elastromeric retractive materials can comprise without limitation LYCRA® materials, elastomeric materials including latex or rubber or synthetic urethanes, or the like, and laminates thereof. In particular embodiments, the retractive material can comprise an elastomeric material having an unstable state relative to some other stable and elastic state. In such embodiments, the retractive material can, but need not, have elastomeric properties in the unstable state. Other examples include heat-shrinkable elastic materials such as described in U.S. Pat. No. 4,816,094 issued Mar. 28, 1989 to Pomplun et al., U.S. Pat. No. 4,665,306 issued May 12, 1987 to Roland et al., and U.S. Pat. No. 4,663,106 issued May 5, 1987 to Pomplun et al., all of which are herein incorporated by reference.

The pant 10 can also include an absorbent structure 60. The absorbent structure 60 can be attached to the garment shell 64 at the front waist edge 38 and back waist edge 39, or at some point below the front waist edge 38 and back waist edge 39 on the front region 22 and back region 24. Alternatively, the absorbent structure 60 can be attached to the garment shell 64 in the crotch region 26.

Any suitable absorbent structure can be used for the absorbent structure 60. The absorbent structure 60 can be any structure which is generally compressible, conformable, non-irritating to the skin, and capable of absorbing and retaining liquids and certain body wastes. The absorbent structure 60 can be manufactured in a wide variety of sizes and shapes, from a wide variety of liquid absorbent materials commonly used in the art, and may be stretchable, non-stretchable, or elastic. For example, the absorbent structure 60 can suitably include a matrix of hydrophilic fibers, such as a web of cellulosic fluff, mixed with particles of a high-absorbency material commonly known as superabsorbent material. In a particular embodiment, the absorbent structure 60 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 60 to better contain and absorb body exudates. The concentration of the superabsorbent particles can also vary through the thickness of the absorbent structure 60. Alternatively, the absorbent structure 60 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent structure 60 includes a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent structure 60 in an amount of from 0 to about 90 weight percent based on total weight of the absorbent assembly. The absorbent structure 60 suitably has a density within the range of about 0.10 to about 0.35 grams per cubic centimeter. The absorbent structure 60 may or may not be wrapped or encompassed by a suitable wrap that may help maintain the integrity and/or shape of the absorbent assembly.

The absorbent structure 60 can also incorporate other materials that are designed primarily to receive, temporarily store, and/or transport liquid along the mutually facing surface with absorbent structure 60, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C. U.S.A.

In particular embodiments, the absorbent structure 60 is thin to provide a slim, comfortable, non-bulky pant 10. Any suitable thin absorbent structure may be used, such as for example, the thin absorbent described in WO 02/49565, published Jun. 27, 2002, by Sawyer et al., which is incorporated herein by reference.

The absorbent structure 60, desirably although not necessarily, includes a pair of containment flaps 62 (FIGS. 1 and 7) which are configured to provide a barrier to the transverse flow of body exudates. A flap elastic member (not shown) can be operatively joined with each containment flap 62 in any suitable manner as is well known in the art. The elasticized containment flaps 62 define an unattached edge which assumes an upright, generally perpendicular configuration in at least the crotch region 26 of the pant 10 to form a seal against the wearer s body. Suitable constructions and arrangements for the containment flaps 62 are generally well known to those skilled in the art and are described in U.S. Pat. No. 4,704,116 issued Nov. 3, 1987 to Enloe, which is incorporated herein by reference.

In the alternative, a pant-like garment insert could be used for the absorbent structure 60. For example, the pant-like garment insert suitably includes a body side liner, an outer cover, an absorbent assembly between the body side liner and the outer cover, and side panels. Example of suitable inserts include a training pant, such as HUGGIES® PULL-UPS® Disposable Training Pants, and disposable underpants, such as GOODNIGHTS® Disposable Underpants, both manufactured by Kimberly-Clark Corporation, Neenah, Wis., U.S.A.

As another alternative, a pad-type absorbent could be used for the absorbent structure. The pad-type absorbent can be attached in the crotch-region 26 of the pant 10. An example of a suitable pad-type absorbent is a feminine care pad such as KOTEX® Feminine Napkins, KOTEX® LIGHTDAYS® Pantiliners, or an incontinence absorbent pad such as POISE® Feminine Guards and Pads or DEPEND® Guards for Men, all manufactured by Kimberly-Clark Corporation, Neenah, Wis., U.S.A.

The garment shell 64 is desirably constructed of materials which are comfortable against the skin and non-irritating. It is contemplated that the garment shell 64 can be either disposable or durable, i.e., launderable, in the embodiments without an absorbent structure, and disposable in the embodiments with an absorbent structure. Both nonwoven and woven materials are contemplated for the garment shell 64. For example, the garment shell 64 for pant 10 can be selected from a wide variety of materials, including elastic, stretchable, or nonstretchable materials. Any other type of nonwoven laminate known to those skilled in the art can also be used. The garment shell 64 can be a single layer of material or a multi-layered laminate structure. Suitable materials for the garment shell 64 include stretchable nonwovens, non-strechable nonwovens, and nonwoven laminates including spandex and/or stretchable film. Spandex is any of various elastic textile fibers made chiefly of polyurethane. LYCRA® is a brand of spandex commercially available from E.I. du Pont de Nemours and Company, Wilmington, Del., U.S.A. Meltblown laminates are a suitable type of nonwoven laminate. The garment shell 64 may also be made of those materials of which the absorbent structure 60 is made. It is desired that the garment shell 64 provides a relatively cloth-like texture to the wearer. The material for the garment shell 64 desirably, although not necessarily, has the ability to drape and conform to some extent to the body. In addition, the material can, but need not, be opaque.

Figure 2:
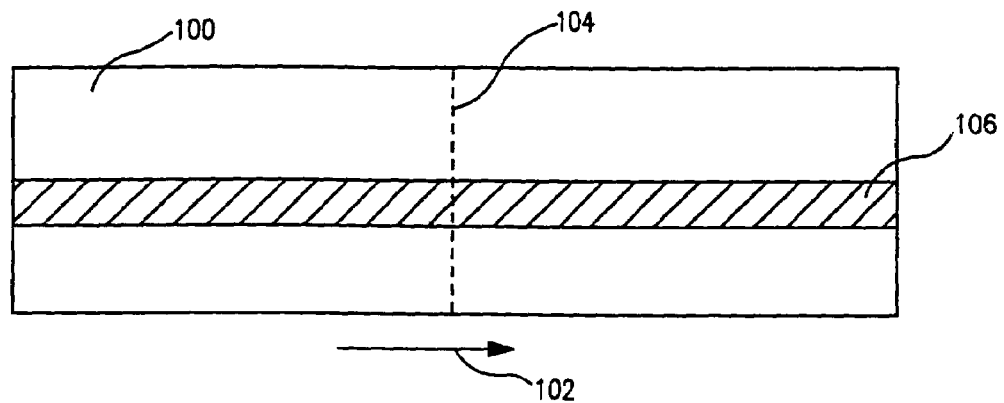
FIG. 2 is a top view of a flat web including a strip substantially aligned along the machine direction center line.

The present invention also includes various methods for making pants having a front-to-back crotch seam from a flat web, as shall now be explained and illustrated. Referring to FIG. 2, a single flat web 100 is provided in the machine direction, represented by arrow 102. In the alternative, a flat web that is folded in half (not shown) in the machine direction can be used for the flat web 100. As another alternative, two webs that are joined at their edges to form a double-width piece (not shown) can be used for the flat web 100. The flat web 100 can be composed of any material previously described for the garment shell 64.

Figure 2A:
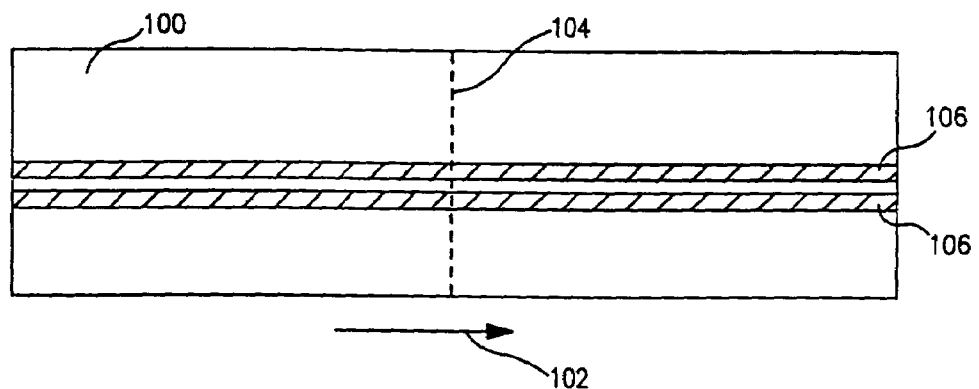
FIG. 2A is a top view of a flat web according to another embodiment of the invention.

In particular embodiments, the flat web 100 includes a strip 106 substantially aligned along the machine direction center line. In these embodiments the strip 106, as more fully described below, becomes the waist elastic member 58, and can be a delayed retraction material. The strip 106 can be layered over and attached to the flat web 100 by any suitable method. Such methods include adhesive bonding, ultrasonic bonding, thermal bonding, or the like. As another alternative, the strip 106 can be placed between and bonded to two flat web pieces of material by any suitable method. As another alternative, two strips 106 can be placed on either side of the machine direction center line as shown in FIG. 2A. The non-retractive area along the machine direction center line can assist in reducing process variability due to oscillating of the web as the slits 126 (described in more detail below with respect to FIG. 4) are made. By leaving the non-retractive area along the machine direction center line between the two strips of delayed retraction material, the size of the eventual waist elastic 58 can be manufactured consistently.

Figure 3:
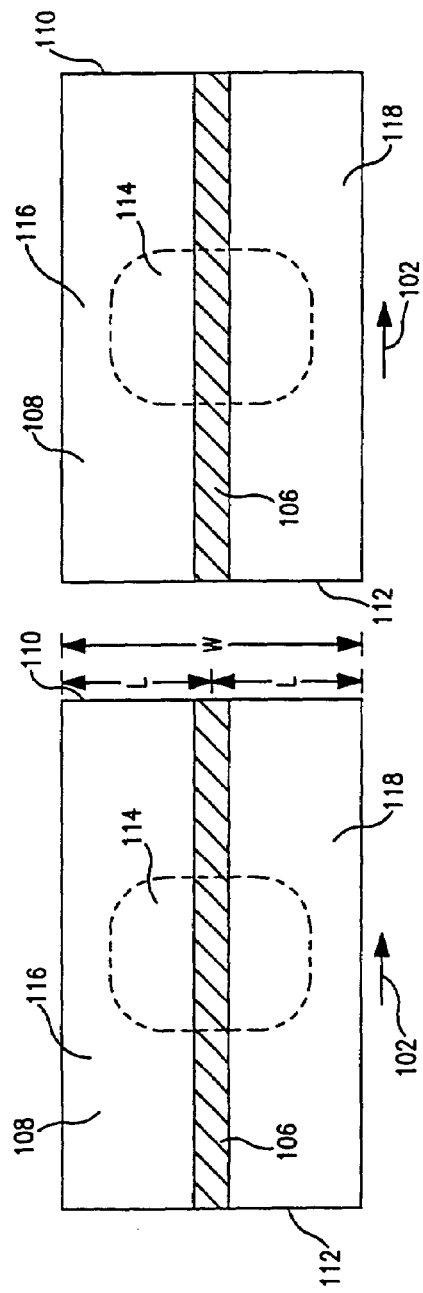
FIG. 3 shows separate pieces which have been cut from the flat web in FIG. 2.

In particular embodiments, flat web 100 can be cut along cut line 104 into separate pieces 108. (FIG. 3). The cutting can be accomplished, for example, using a cutting roll (not shown). Alternatively, any other suitable cutting method known in the art can be used. As another alternative, the separate pieces 108 could be provided as pre-cut pieces so that this cutting step could be skipped, and the process could start with the separate piece as the flat web.

Figure 2B:
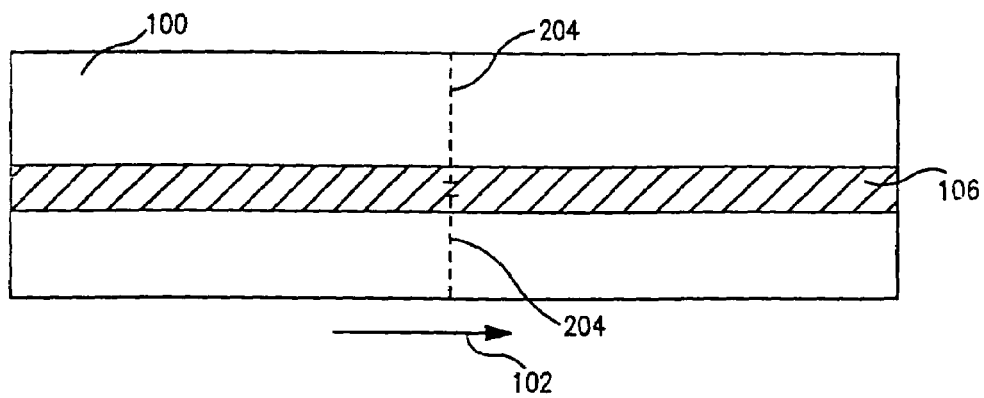
FIG. 2B is a top view of a flat web showing the cut lines to prepare interconnected pieces according to another embodiment of the invention.
Figure 3A:
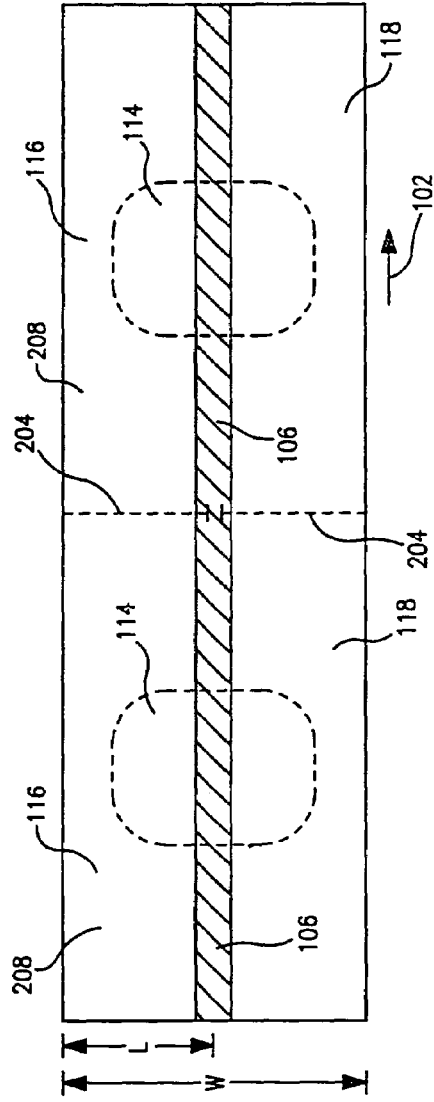
FIG. 3A shows interconnected pieces according to the embodiment shown in FIG. 2B.

As another alternative, in particular embodiments, the flat web 100 can be cut along cut lines 204 into interconnected pieces 208 (FIGS. 2B and 3A). The cutting can be accomplished, for example, using a cutting roll (not shown). Any other suitable cutting method known in the art can be used. Each cut line 204 includes two segments which leave an uncut or connected area which acts to maintain a connection between the interconnected pieces 208.

Each separate piece 108, or interconnected piece 208, as more fully described below, becomes a garment shell 64. The width W (FIGS. 3 and 3A) of each separate piece 108 and interconnected piece 208 (as well as of the flat web 100) must be about twice the desired length L of the pant 10 (FIGS. 1, 3 and 3A). Each separate piece 108 defines a leading edge 110, a trailing edge 112, a center portion 114 (shown within and defined by the dotted lines in FIG. 3), a first side portion 116 and a second side portion 118. Each interconnected piece 208 defines a center portion 114 (shown within and defined by the dotted lines in FIG. 3A), a first side portion 116 and a second side portion 118. The center portion 114 of each separate piece 108 or interconnected piece 208 is a generally rectangular shape with square or curved corners, located between the leading edge 110 and the trailing edge 112 with the shorter sides of the rectangle running in the machine direction as shown in FIGS. 3 and 3A. Alternatively, the center portion 114 can be any desired shape.

Figure 4:
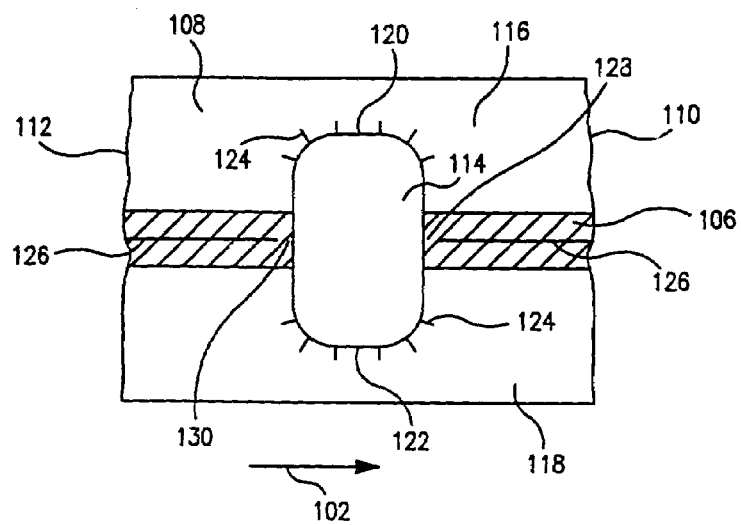
FIG. 4 shows one of the separate pieces from FIG. 3 with the center portion removed and slits cut along the machine direction center line and also slits along the first seam edge and the second seam edge.
Figure 4A:
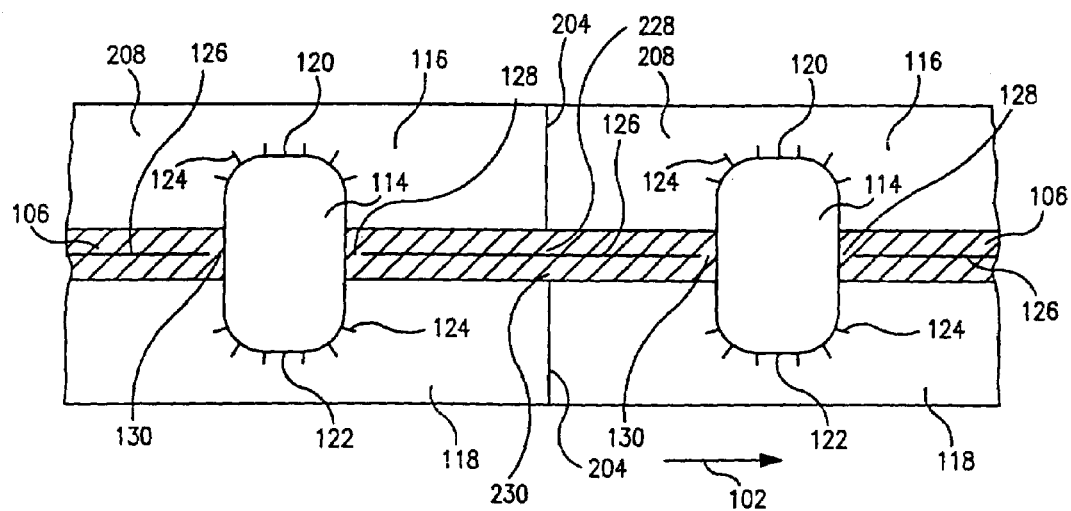
FIG. 4A shows the interconnected pieces from FIG. 3A with the center portions removed and a slit along the machine direction center line and also slits along the first seam edges and the second seam edges.

Referring to FIGS. 4 and 4A, the center portion 114 of each separate piece 108 or interconnected piece 208 is cut out of each separate piece 108 or each interconnected piece 208. The cutting can be accomplished, for example, using a rotary die cutter, a reciprocating die cutter, a water cutter or a laser (not shown). Alternatively, any other suitable cutting method known in the art can be used. This step of cutting out the center portion 114 can, as explained and illustrated here, be performed after the step of cutting the flat web 100 into separate pieces 108 or into interconnected pieces 208. In the alternative, it is also contemplated that the step of cutting the flat web 100 into separate pieces 108 or interconnected piece 208 can be performed after the step of cutting out the center portions 114. Following cutting out the center portion 114 and separating the center portion 114 from each separate piece 108 or interconnected piece 208, any trim can be removed if necessary by vacuum (not shown) or other methods known in the art. Cutting out the center portion 114 defines a first seam edge 120 and a second seam edge 122.

Slits 124 can be cut along the first seam edge 120 and second seam edge 122 desirably at least in the corners adjacent the rectangular center portion 114. (FIGS. 4 and 4A). The slits 124 can be made, for example, by a rotary die cutter, a reciprocating die cutter, a water cutter or a laser, or by any other method known in the art.

Referring to FIGS. 4 and 4A, slits 126 can be cut along the machine direction center line in the strip 106. In the embodiment with separate pieces 108, one of the slits 126 is cut from the leading edge 110 toward the center portion 114, and another slit 126 is cut from the trailing edge 112 toward the center portion 114. In the embodiment with the interconnected pieces 208, slit 126 can be cut along the machine direction center line of the interconnected pieces 208 so that there is a single slit running from a second attached segment 130 on one interconnected piece 208 to a first attached segment 128 on an adjacent interconnected piece 208. Specifically, the first and second attached segments 128 and 130 refer to the unslit regions between slit 126 and the removed center portion 114. The slits 126 can be made, for example, by a rotary die cutter, a reciprocating die cutter, a water cutter or a laser, or by any other method known in the art. In addition, referring to FIG. 4A, slits can also be cut along cut lines 204 using any one of the previously mentioned techniques.

In the embodiment with separate pieces 108, the slits 126 and the removed center portion 114 together define a first attached segment 128 and a second attached segment 130 (FIG. 4). Specifically, the first and second attached segments 128 and 130 refer to the unslit regions between slit 126 and the removed center portion 114. If the flat web 100 was folded in half (not shown) in the machine direction, each separate piece 108 can be unfolded at this point before continuing (not shown).

Figure 5:
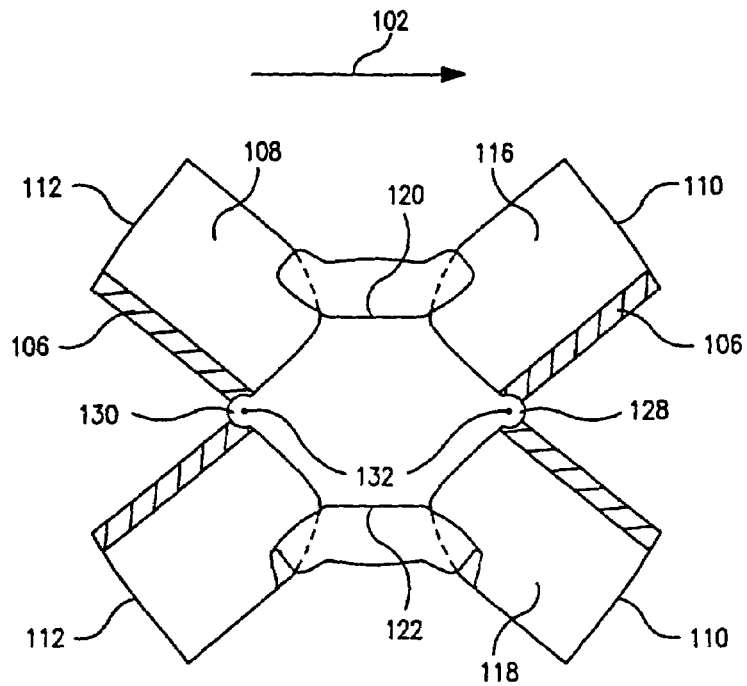
FIG. 5 shows the attached segments of the separate piece of FIG. 4 being drawn away from each other.

Referring to FIG. 5, in the embodiment with separate pieces 108, the first and second attached segments 128 and 130 are drawn away from each other in opposite directions. Drawing the first and second attached segments 128 and 130 away from each other can be accomplished by pins 132 that run on chains (not shown) underneath the separate pieces 108. Alternatively, it is contemplated that the pins 132 could be positioned above the separate pieces 108. The pins 132 can be, for example, retractable pins described in U.S. Pat. Nos. 4,786,346 and 4,946,539, to Ales et al., both of which are herein incorporated by reference, or other suitable devices known to one skilled in the art. For example, two pins 132 that move at different speeds (i.e., that are attached to different drive chains) could be used to separate the first and second attached segments 128 and 130 from one another. The pins 132 would need to travel for some distance at the same speed, to maintain the desired pin separation while the crotch seam is formed. In alternative embodiments, the first and second attached segments 128 and 130 can be drawn away from each other by means other than pins.

As shown in FIGS. 5 and 6, drawing the first and second attached segments 128 and 130 away from each other in opposite directions brings the first and second seam edges 120 and 122 together along the machine direction center line. Portions of the first and second side portions 116 and 118 may become folded (as illustrated by the dotted lines in FIGS. 5 and 6) as the first and second seam edges 120 and 122 are brought together.

The first and second seam edges 120 and 122 are brought together by either being overlapped or raised into a facing relation to eventually form either a lap seam or a fin seam, as are known in the art, for the crotch seam 56 along the machine direction center line. This may be achieved by supplying a jet or curtain of air against the first and second seam edges 120 and 122. The jet or curtain of air can be supplied by an air handling apparatus (not shown) such as air knives, nozzles, or the like. Other suitable apparatuses known in the art may be used. The shapes of the pins 132 may also contribute to positioning the first and second seam edges 120 and 122 into an overlapping or facing relationship.

Referring to FIG. 6, the crotch seam 56 (FIG. 7) is formed by bonding first and second seam edges 120 and 122 along the machine direction center line to form the garment shell 64. This bonding can be accomplished by using ultrasonic or thermal bonding wheels rotating in a facing relationship just above or below the surface of each separate piece 108 to form the crotch seam 56. For example, an anvil wheel 134 and a horn wheel 136 defining a nip 142 and rotating in the directions of arrows 138 can be used to bond the first and second seam edges 120 and 122 to form crotch seam 56. Alternatively, any suitable bonding method known in the art can be used, such as adhesives, sewing or the like. The pins 132 can then be withdrawn and travel back underneath (or over) the garment shell 64 to prepare for a subsequent separate piece 108. The front-to-back crotch seam 56 thus formed will run along the midline of the wearer's body. As shown in FIG. 6, the front region 22 passes through the bonding wheels first. It is also contemplated that the back region 24 can pass through the bonding wheels first.

Referring to FIG. 4A, in the embodiment with interconnected pieces 208, the slit 126 and the removed center portion 114 together define a first attached segment 128 and a second attached segment 130, located between the first and second seam edges 120, 122. Specifically, the first and second attached segments 128 and 130 refer to the unslit regions between slit 126 and the removed center portion 114. The slit 126 also defines a third attached segment 228 and a fourth attached segment 230, located on either side of the slit 126 which now divides the uncut or connected area between the interconnected pieces 208. Specifically, the third and fourth attached segments 228 and 230 refer to the intact regions between the slits along cut lines 204 and the slit 126. If the flat web 100 was folded in half (not shown) in the machine direction, the interconnected pieces 208 can be unfolded at this point before continuing (not shown).

Figure 5A:
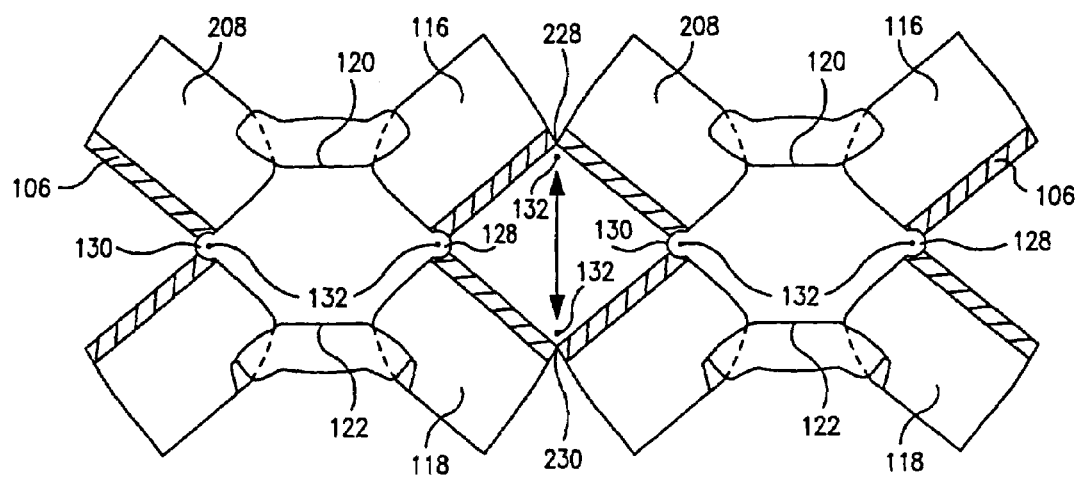
FIG. 5A shows the attached segments of interconnected pieces of FIG. 4A being drawn away from each other.

Referring to FIG. 5A, the first and second attached segments 128 and 130 on what will become a single garment shell 64 are drawn away from each other in opposite directions. In addition, and simultaneously, the third and fourth attached segments 228 and 230 are drawn away from each other in opposite directions. Drawing the first and second attached segments 128 and 130 away from each other and drawing the third and forth attached segments 228 and 230 can be accomplished by pins 132 that run on chains or conveyors (not shown) underneath the interconnected pieces 208. Alternatively, it is contemplated that the pins 132 could be positioned above the interconnected pieces 208. The pins 132 can be, for example, retractable pins described in U.S. Pat. Nos. 4,786,346 and 4,946,539 to Ales et al, both of which are herein incorporated by reference, or other suitable devices known to one skilled in the art. For example, two pins 132 that move at different speeds (i.e., that are attached to different drive chains) could be used to separate the first and second attached segments 128 and 130 from one another. The pins 132 used to separate first and second attached segments 128 and 130 would need to travel for some distance at the same speed, to maintain the desired pin separation while the crotch seam is formed. In alternative embodiments, the first and second attached segments 128 and 130, and third and fourth attached segments 228 and 230, can be drawn away from each other by means other than pins.

As shown in FIGS. 5A and 6A, drawing the first and second attached segments 128 and 130 away from each other in opposite directions brings the first and second seam edges 120 and 122 together along the machine direction center line. Portions of the first and second side portions 116 and 118 may become folded (as illustrated by the dotted lines in FIGS. 5A and 6A) as the first and second seam edges 120 and 122 are brought together. In addition, drawing the third and fourth attached segments 228 and 230 away from each other in opposite directions rotates segments of the interconnected pieces 208 at the same time that interconnected garment shells 64 (FIG. 6A) continue to travel in the direction of arrow 102. The interconnected garment shells 64 (prior to formation of the crotch seam 56) at this point are still connected by the third and fourth attached segments 228 and 230. As shown in FIG. 6A, the front region 22 passes through the bonding wheels first. It is also contemplated that the back region can pass through the bonding wheels first.

The first and second seam edges 120 and 122 are brought together by either being overlapped or raised into a facing relation to eventually form either a lap seam or a fin seam, as are known in the art, for the crotch seam 56 along the machine direction center line. This may be achieved by supplying a jet or curtain of air against the first and second seam edges 120 and 122. The jet or curtain of air can be supplied by an air handling apparatus (not shown) such as air knives, nozzles, or the like. Other suitable apparatuses known in the art may be used. The shapes of the pins 132 may also contribute to positioning the first and second seam edges 120 and 122 into an overlapping or facing relationship. The crotch seam is formed as described above with respect to FIG. 6. The interconnected garment shells 64 can be cut apart by cutting the third and fourth attached segments 228 and 230 to form separate garment shells 64.

Referring to FIGS. 6 and 6A, as previously mentioned, the separate piece 108 or interconnected piece 208 has now become the garment shell 64 prior to formation of the side seams 54. As shown and as previously mentioned with respect to FIG. 1, the garment shell 64 can include a front region 22, a back region 24, a crotch region 26, an inner surface 28, and an outer surface 30, front waist edge 38, back waist edge 39, and waist elastic member 58. The bonding together of first and second seam edges 120 and 122, as previously described, forms the front-to-back crotch seam 56. It is also contemplated that the garment shell 64 can be made upside-down, i.e., with the inner surface 28 facing downwardly (not shown) with the pins 132 positioned above or below the separate pieces 108 or interconnected pieces 208 and the bonding wheels 134 and 136 positioned below the garment shell 64 (or interconnected garment shells 64) during formation of the crotch seam 56.

When made without an absorbent structure, the garment shell 64 can then be folded and the side seams 54 formed by any conventional method known in the art to form a closed pant 10 (without an absorbent structure).

In particular embodiments, the waist elastic member 58 can include any of the previously described suitable materials. In these embodiments, the waist elastic members 58 can be attached to the pant 10 by any method known in the art at any point in the manufacturing process, and need not start out as strip 106 on the flat web as previously described. Such methods include adhesive bonding, ultrasonic bonding, or the like. As one example, the waist elastic member 58 can be attached after the garment shell 64 is assembled, as described, for example in U.S. Patent Publication No. U.S. 2002/0084017, published Jul. 4, 2002, by Rabe et al., herein incorporated by reference.

Figure 7:
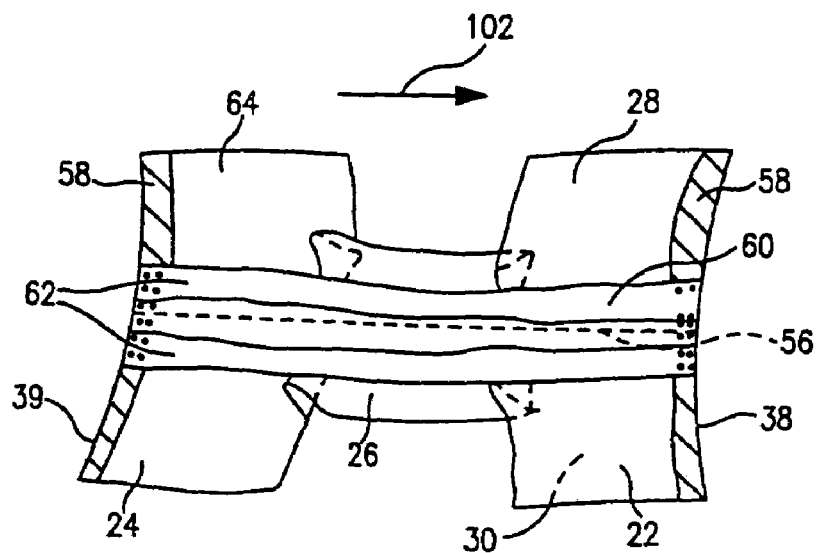
FIG. 7 illustrates the garment shell including an absorbent structure according to one embodiment of the invention.
Figure 8:
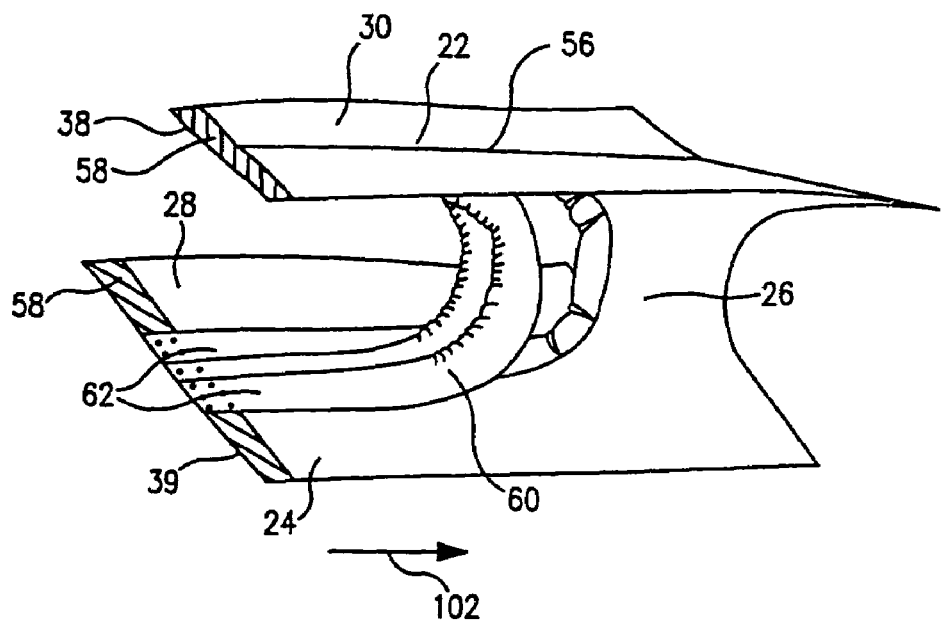
FIG. 8 illustrates the garment shell including an absorbent structure with the garment shell in the folded position prior to forming the side seams.

Referring to FIG. 7, in particular embodiments, an absorbent structure 60 is included in the pant 10. The absorbent structure 60 can be introduced into the pant 10 in any suitable manner known in the art. In particular embodiments, the absorbent structure 60 can be placed on top of the crotch seam 56 on the inner surface 28 of the garment shell 64. The absorbent structure 60 can be attached to the garment shell 64 at the front waist edge 38 and back waist edge 39 (FIGS. 7 and 8), or at some point below the front waist edge 38 and back waist edge 39 on the front region 22 and back region 24. The attachment can be accomplished by ultrasonic or adhesive bonding, or any other suitable method known in the art. As shown in FIG. 8, attachment to the front and back regions 22 and 24 provides for a loose fit of the garment shell 64 in the crotch region 26, while still maintaining a close fit of the absorbent structure 60 to the body of the wearer. In particular embodiments, the absorbent structure 60 is stretchable in order to provide the desired close to the body fit for the absorbent structure 60 while the garment shell 64 hangs loosely. Alternatively, a slight longitudinal gathering of the garment shell 64 may be required to provide a relatively loose fit for the garment shell 64.

The garment shell 64 with the absorbent structure 60 can then be folded as shown in FIG. 8 and the side seams 54 formed by any conventional method known in the art to form the pant 10, as shown in FIG. 1. After folding of the garment shell 64 and formation of the side seams 54 (with or without an absorbent structure 60), if a temporarily inhibited elastic is used as the strip 106 (and thus the waist elastic member 58), it may need to be activated to restore the elasticity.

The various components of the pant can be connected together by any means known to those skilled in the art such as, for example, adhesive, thermal and/or ultrasonic bonds, and also sewing and other methods used in durable garment manufacturing. Desirably, most of the components are connected using ultrasonic bonding for improved manufacturing efficiency and reduced raw material costs. For example, in particular embodiments, the crotch seam 56 and the side seams 54 are made using ultrasonic bonding. Certain garment manufacturing equipment which is readily known and understood in the art, including frames and mounting structures, ultrasonic and adhesive bonding devices, transport conveyors, transfer rolls, guide rolls, tension rolls, and the like, have not been shown in the Figures.

Figure 9:
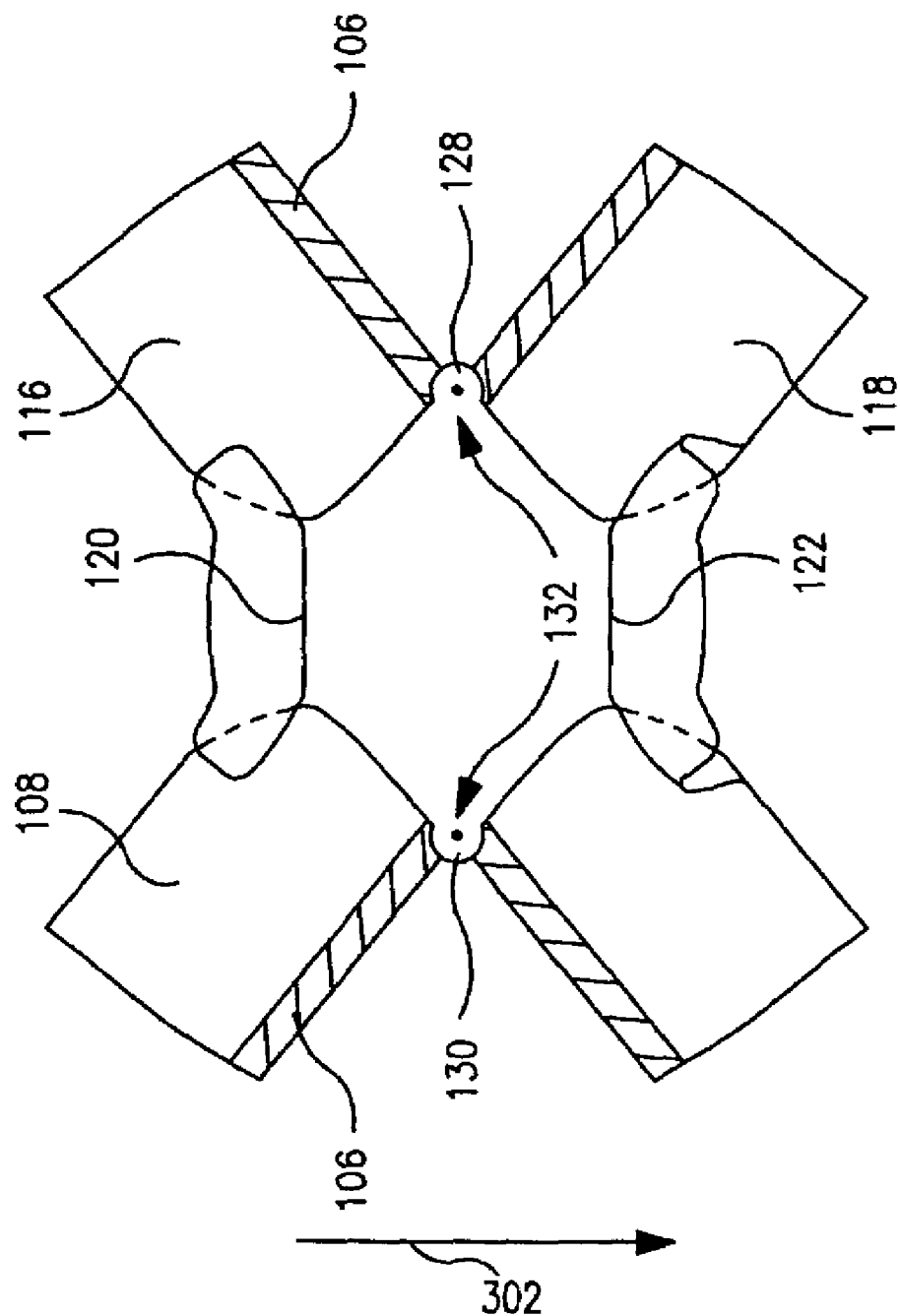
FIG. 9 shows the attached segments of the separate piece being drawn away from each other as the separate piece travels in the cross-machine direction.
Figure 10:
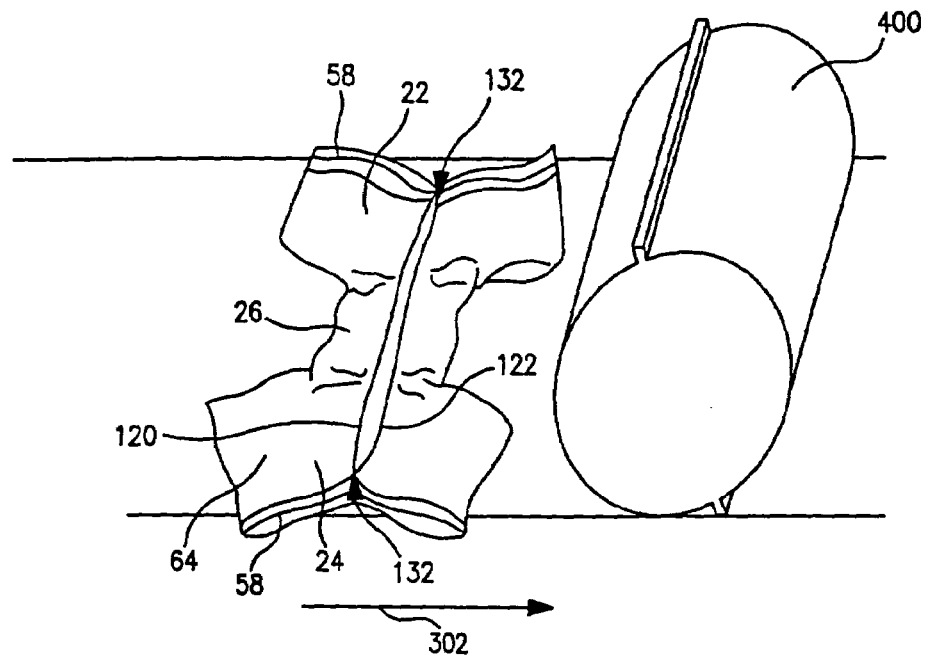
FIG. 10 illustrates the garment shell according to one embodiment of the invention as the garment shell travels in the cross-machine direction prior to formation of the crotch seam.
Figure 11:
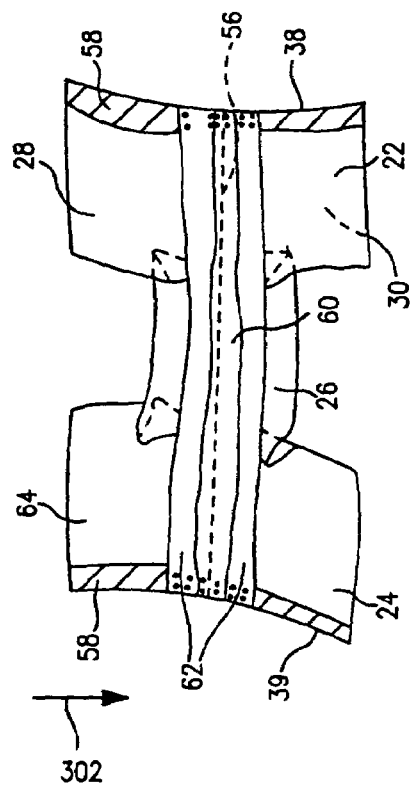
FIG. 11 illustrates the garment shell including an absorbent structure as the garment shell travels in the cross-machine direction according to another embodiment of the invention.

This method for making pants can be carried out using machine direction assembly as shown, or alternatively in any other manner using high speed and/or automated garment manufacturing processes, especially those in which a continuous flat web is used to form individual, discrete articles. For example, the method for making pants can also be carried out using cross-machine direction assembly. The cross-machine direction process can be initiated by providing a flat web and following the steps described above with respect to FIGS. 2–4 for the embodiment with separate pieces 108. The first and second attached segments 128 and 130 can be drawn away from each other as shown in FIG. 9 as each separate piece is traveling in the direction of arrow 302. Referring to FIG. 10, the crotch seam 56 (not shown) is formed by bonding first and second seam edges 120 and 122 along the midline of the garment to form the garment shell 64. This bonding may be accomplished by, for example, a rotary sealing apparatus 400 with intermittent bonding capability such as that shown in FIG. 10. Bonds may be ultrasonic, thermal, pressure, or other types known in the art. Alternately, an indexing thermal sealer or adhesive bonding, or other means known in the art, may be used to bond seam edges 120 and 122. The bonding can be accomplished as described above as the garment shell 64 travels in the direction of arrow 302. Referring to FIG. 11, in particular embodiments, an absorbent structure 60 is included in the pant 10. The absorbent structure 60 can be introduced into the pant 10 in any suitable manner known in the art as the garment shells travel in the direction of arrow 302.

The cross-machine direction process can also be carried out using interconnected pieces in a manner similar to that previously described for the machine direction process. The interconnected cross-machine direction process can be initiated by providing a flat web and following the steps described above for the embodiment with interconnected pieces in the machine direction with respect to FIGS. 3A, 4A, 5A and 6A, with some minor modifications as explained and illustrated.

Figure 12:
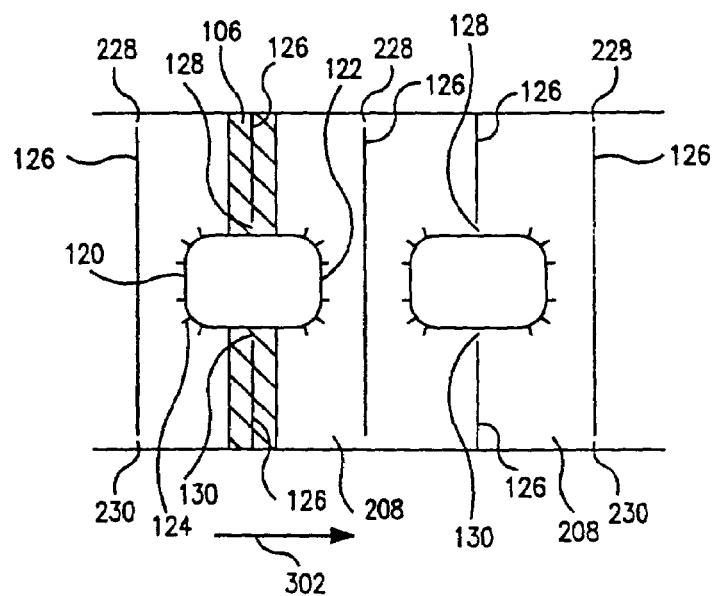
FIG. 12 shows interconnected pieces according to another embodiment of the invention.

Referring to FIG. 12, in the cross-machine direction embodiment with interconnected pieces 208, the slits 126 and the removed center portion together define a first attached segment 128 and a second attached segment 130, located between the first and second seam edges 120, 122. Slits 126 also define a third attached segment 228 and a fourth attached segment 330.

Figure 13:
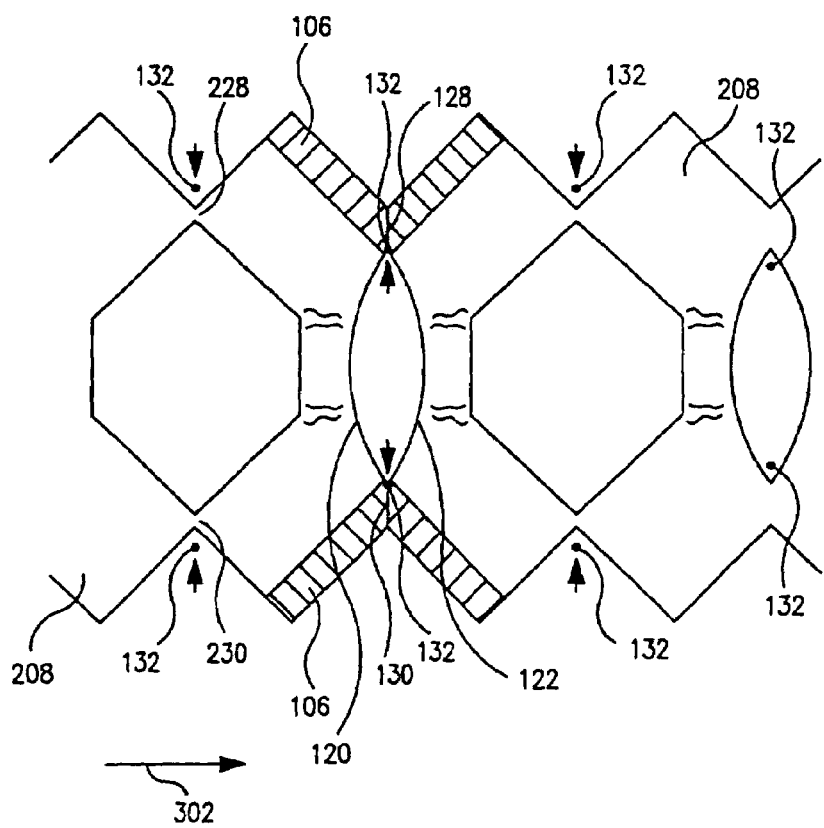
FIG. 13 shows the first and second attached segments being drawn away from each other and the third and fourth attached segments being drawn towards each other for the embodiment shown in FIG. 12.

Referring to FIG. 13, the first and second attached segments 128 and 130 are drawn away from each other in opposite directions as illustrated by the arrows. In addition, and simultaneously, the third and fourth attached segments 228 and 230 are pushed towards each other as also illustrated by the arrows. Drawing the first and second attached segments 128 and 130 away from each other and pushing the second and third attached segments 228 and 230 towards each other can be accomplished by pins 132 that run on chains or conveyors (not shown) underneath the interconnected pieces 208. Alternatively, it is contemplated that the pins 132 could be positioned above the interconnected pieces 208. The pins 132 can be, for example, retractable pins previously described, or other suitable devices known to one skilled in the art. In alternative embodiments, the first and second attached segments 128 and 130 can be drawn away from each other, and third and fourth attached segments 228 and 230 can be pushed towards each other, by means other than pins.

As shown in FIGS. 12 and 13, drawing the first and second attached segments 128 and 130 away from each other in opposite directions brings the first and second seam edges 120 and 122 together. In addition, drawing the third and fourth attached segments 228 and 230 towards each other rotates the interconnected pieces 208 so that interconnected garment shells (not shown) would continue to travel in the direction of arrow 302. The interconnected garment shells (prior to formation of the crotch seam 56) at this point would still be connected by the third and fourth attached segments 228 and 230.

The first and second seam edges 120 and 122 are brought together by either being overlapped or raised into a facing relation to eventually form either a lap seam or a fin seam, as are known in the art, for the crotch seam 56. As previously described with respect to the machine direction interconnected process, this may be achieved by supplying a jet or curtain of air against the first and second seam edges 120 and 122. The jet or curtain of air can be supplied by an air handling apparatus (not shown) such as air knives, nozzles, or the like. Other suitable apparatuses known in the art may be used. The shapes of the pins 132 may also contribute to positioning the first and second seam edges 120 and 122 into an overlapping or facing relationship. The crotch seam is formed as previously described above with respect to FIG. 10. The interconnected garment shells can be cut apart by cutting the third and fourth attached segments 228 and 230 to form separate garment shells 64. In particular embodiments an absorbent structure can be included and introduced in any suitable manner as the garment shells travel in the direction of arrow 302.

Figure 14:
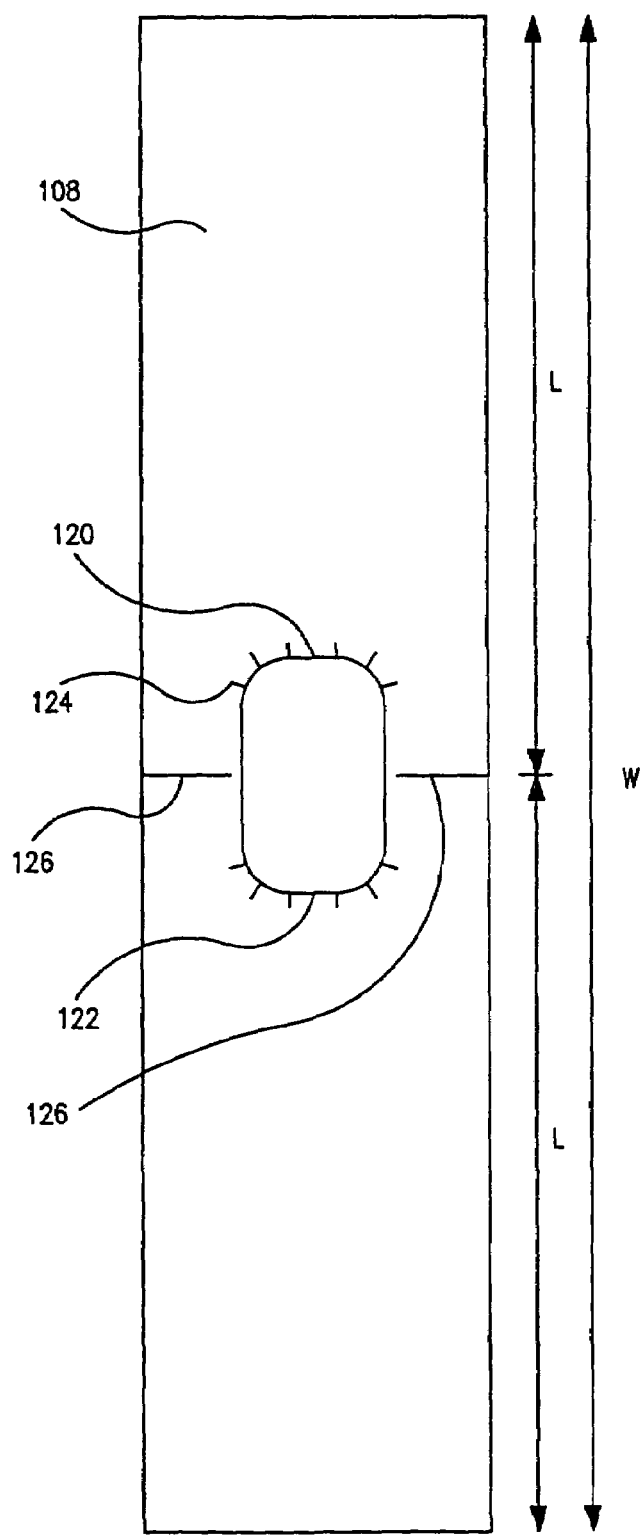
FIG. 14 illustrates an embodiment in which the flat web has been modified to accommodate full length pants.

It is contemplated that the method of the present invention could also be used to make full length pants. In this embodiment, the length of the flat web can be adjusted to accommodate the eventual length of the pants, as shown for example in FIG. 14.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of making a pant having a front-to-back crotch seam, comprising:
    providing a flat web defining a center portion;
    cutting out the center portion of the flat web to define a first seam edge and a second seam edge;
    cutting at least one slit in the flat web to define a first attached segment, and at least one slit to define a second attached segment;
    drawing the first and second attached segments away from each other;
    bringing the first seam edge toward the second seam edge;
    bonding the first and second seam edges together to form the crotch seam and a garment shell; and
    attaching a front region of the garment shell to a back region of the garment shell to form at least two side seams to form the pant.

2. The method of claim 1, wherein the flat web includes at least one delayed retraction material.

3. The method of claim 1, further comprising cutting at least one slit in at least one of the first seam edge and the second seam edge.

4. The method of claim 1, wherein drawing the first and second attached segments away from each other comprises positioning pins under or over the flat web between the first and second seam edges and moving the pins away from each other.

5. The method of claim 1, wherein bringing the first seam edge toward the second seam edge comprises supplying air against at least one of the first seam edge and the second seam edge.

6. The method of claim 1, wherein bonding the first and second seam edges together comprises using one of ultrasonic wheels and thermal wheels.

7. The method of claim 1, further comprising cutting a larger piece of material to provide a separate piece, the separate piece acting as the flat web.

8. The method of claim 1, wherein the method is carried out using machine direction assembly.

9. The method of claim 1, wherein the method is carried out using cross-machine direction assembly.

10. The method of claim 1, further comprising cutting a larger piece of material to provide interconnected pieces, each interconnected piece acting as the flat web.

11. A method of making an absorbent pant having a front-to-back crotch seam, comprising:
    providing a flat web defining a center portion;
    cutting out the center portion of the flat web to define a first seam edge and a second seam edge;
    cutting at least one slit in the flat web to define a first attached segment, and at least one slit to define a second attached segment;

drawing the first and second attached segments away from each other;

bringing the first seam edge toward the second seam edge;

bonding the first and second seam edges together to form the crotch seam and a garment shell;

attaching an absorbent structure to the garment shell covering the crotch seam on an inner surface of the garment shell; and attaching a front region of the garment shell to a back region of the garment shell to form at least two side seams to form the pant.

12. The method of claim 11, wherein the flat web includes at least one delayed retraction material.

13. The method of claim 11, further comprising cutting at least one slit in at least one of the first seam edge and the second seam edge.

14. The method of claim 11, wherein drawing the first and second attached segments away from each other comprises positioning pins under or over the flat web between the first and second seam edges and moving the pins away from each other.

15. The method of claim 11, wherein bringing the first seam edge toward the second seam edge comprises supplying air against at least one of the first seam edge and the second seam edge.

16. The method of claim 11, wherein bonding the first and second seam edges together comprises using one of ultrasonic wheels and thermal wheels.

17. The method of claim 11, further comprising cutting a larger piece of material to provide a separate piece, the separate piece acting as the flat web.

18. The method of claim 11, wherein the method is carried out using machine direction assembly.

19. The method of claim 11, wherein the method is carried out using cross-machine direction assembly.

20. The method of claim 11, further comprising cutting a larger piece of material to provide interconnected pieces, each interconnected piece acting as the flat web.

* * * * *